US007685893B2

(12) United States Patent
Champseix et al.

(10) Patent No.: US 7,685,893 B2
(45) Date of Patent: Mar. 30, 2010

(54) SYRINGE BLOCK FOR AUTOMATIC MACHINE FOR ANALYSIS OF LIQUIDS, IN PARTICULAR FOR BLOOD ANALYSIS

(75) Inventors: Serge Champseix, Tarnac (FR); Henri Champseix, Saint Gely du Fesc (FR)

(73) Assignee: C2 Diagnostics, Montpellier (FR)

( * ) Notice: Subject to any disclaimer, the term of this patent is extended or adjusted under 35 U.S.C. 154(b) by 63 days.

(21) Appl. No.: 10/578,688

(22) PCT Filed: Oct. 22, 2004

(86) PCT No.: PCT/FR2004/002708

§ 371 (c)(1),
(2), (4) Date: May 9, 2006

(87) PCT Pub. No.: WO2005/062015

PCT Pub. Date: Jul. 7, 2005

(65) Prior Publication Data
US 2007/0062314 A1 Mar. 22, 2007

(30) Foreign Application Priority Data
Nov. 18, 2003 (FR) .................................. 03 13452

(51) Int. Cl.
*B01L 3/02* (2006.01)
(52) U.S. Cl. ..................... 73/863.32; 422/73
(58) Field of Classification Search .............. 73/863.32; 422/73, 68.1
See application file for complete search history.

(56) References Cited
U.S. PATENT DOCUMENTS 4,199,013 A  4/1980 Everett et al.
4,231,990 A * 11/1980 Jottier ......................... 422/100
4,254,084 A  3/1981 Blum
4,607,526 A * 8/1986 Bachenheimer et al. ..... 73/865.5
5,648,225 A * 7/1997 Kim et al. .................. 435/7.24
5,988,236 A  11/1999 Fawcett
6,555,065 B1 * 4/2003 Melet ........................... 422/73

FOREIGN PATENT DOCUMENTS

EP          0508495 A    10/1992
EP          0802413 A    10/1997
SU          463027       3/1975
WO          99/26056 A   5/1999

OTHER PUBLICATIONS

International Search Report.
Preliminary French Search Report.

* cited by examiner

*Primary Examiner*—Hezron Williams
*Assistant Examiner*—Mark Shabman
(74) *Attorney, Agent, or Firm*—Young & Thompson

(57) ABSTRACT

A syringe block (1) includes a plurality of syringes (2) and a collector (3), the syringes each having a suction volume, and the collector includes electromagnetic valves. First tubes directly link the electromagnetic valves to the internal volumes and second tubes extend from the electromagnetic valves towards the containers for the sample and/or other liquids, at least one of the syringes being an air pump (15, 16). The syringe block can be used as a support for various components used for the operation thereof, and can be arranged in a climatic condition reproducer. One such syringe block is especially adapted to be used in a liquid analyser, the air pump being used especially to take a sample and/or to drain and clean different recipients containing a sample.

18 Claims, 3 Drawing Sheets

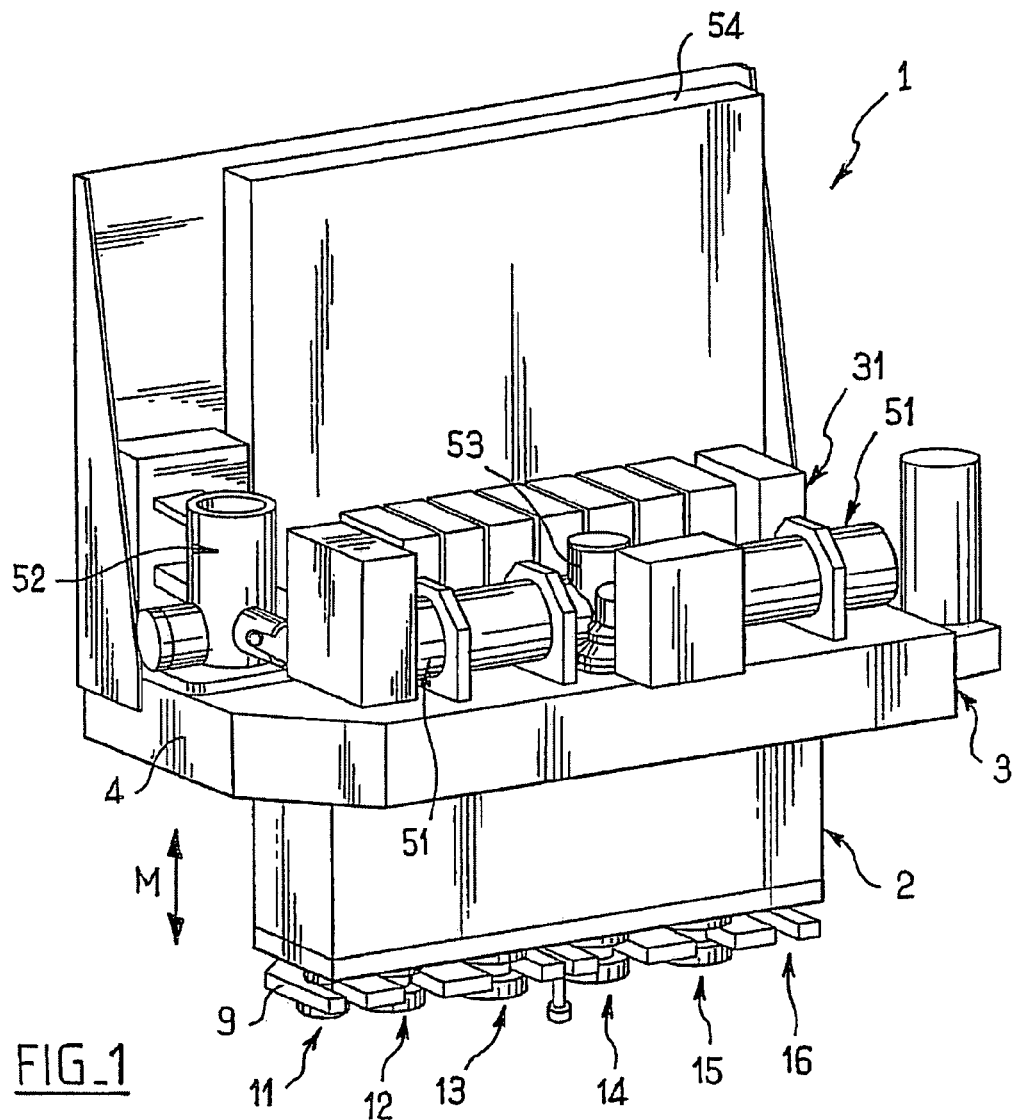
FIG_1
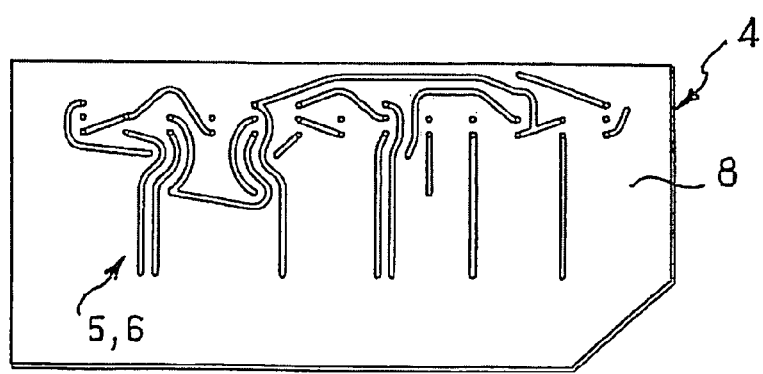
FIG_2

SYRINGE BLOCK FOR AUTOMATIC MACHINE FOR ANALYSIS OF LIQUIDS, IN PARTICULAR FOR BLOOD ANALYSIS

The present invention relates to a syringe block, in other words a set of several syringes, used in an automatic liquid analysis, in particular blood analysis, machine. It also relates to an automatic machine equipped with a syringe block of this kind.

Syringes are an essential element of an automatic analysis machine. They must function in a reliable manner, in particular as regards precise dosage of the liquids to be analyzed or the reactive liquids to be used in analysis. The same applies to the systems connected to the syringes, such as the tubing, the motor systems, the valves and the associated electronics. The risks of breakdown and various leaks which could either distort the analysis or render it impossible should thus be minimized. The realization costs and maintenance times and costs of these automatic machines should also be as low as possible.

With the aim of increasing the reliability of such automatic machines, it has in particular been proposed to reduce the number of motors controlling the movement of the syringes. Thus the document FR 2,815,719 proposes a common motor system for several syringes used for the dosage of the reagents.

However, automatic machines still have numerous disadvantages, in particular that of integrating numerous hydraulic and electric cables between different constituent elements, which entails a cost in particular for their assembly and for their maintenance. Thus, the materials which constitute the hydraulic tubing are particularly sensitive to ageing.

The aim of the invention is to suggest a device allowing the improvement of the reliability of an automatic analysis machine, while simultaneously reducing the assembly and maintenance costs.

According to the invention, such a device is a syringe block, in particular adapted to be used in an automatic liquid-sample analysis machine, said block comprising several syringes and a collector (also called manifold), each syringe comprising a casing and a piston which between themselves define an internal volume, said collector containing electronic switch valves, first ducts linking the electronic switch valves direct to respective internal volumes, variations of which allow the displacement of fluids or liquids used for example by the automatic machine, and second ducts extending from the electronic switch valves to accessories, in particular in the direction of containers for the sample and/or other liquids. Thus, as the syringes are mounted directly on the collector, the hydraulic cabling is limited, and therefore in particular the risks of leaks.

The accessories can advantageously be linked direct to the electronic switch valves by the second ducts or tubing can extend the second ducts between the collector and the accessories.

Advantageously, the syringe block can also comprise an air pump. The air pump can comprise at least one, or more, syringes. This pump can in particular be provided to create a depression in a tank, in order to take a sample with a view to counting in an automatic analysis machine. It can also be provided for the removal by suction of waste, such as liquids which cannot be used, in particular if they have been used in an analysis which has now finished. This waste can also be a rinsing liquid which has been used. The air pump allows waste be sucked from tanks or chambers used for analysis, then disposed of in a dustbin.

The syringe block can comprise one or more parts in which the internal ducts are realized by moulding. Thus, these parts can be made from plastics. The ducts made in this way are in particular not very sensitive to ageing.

The air pump can comprise at least two syringes, operated simultaneously or not, which allows them to give it a large capacity while limiting its bulkiness. Additionally, this means that a smaller casing diameter is possible for each of the syringes forming the pump, and therefore fewer problems of tightness and less work on each of their respective pistons.

Advantageously, the pistons of all the syringes will be rigidly linked to each other such that they simultaneously carry out a single movement inside their respective casings. Thus the electronic switch valves can be arranged in order that the respective unused syringes, although moved simultaneously to a used syringe, aspire then discharge any liquid at the same place, thus carrying out a neutral operation.

The syringe block can additionally comprise certain elements necessary for the functioning of the apparatus into which it is integrated, in particular an automatic analysis machine, these elements being advantageously fixed on the collector, which thus serves as a support. Among these elements can be at least a dilution chamber 52 and/or a measurement chamber 52 and/or an incubation chamber 52 and/or an optical and resistivity measurement circulation vessel 53 and/or an optical bench 51. The dilution chamber, measurement chamber, incubation chamber, an optical and resistivity measurement circulation vessel and/or optical bench may be fixed on the collector and/or linked directly to a respective electronic switch valve by a duct among the second ducts. An element can also be a card carrying electronic circuits, said electronic circuits being used in the analysis where the said block is used in an automatic analysis machine. The card may be fixed on the collector. Thus, integrated into the syringe block, all these elements are close to one another, and in particular to the collector and the valves which distribute the different liquids.

The syringe block can also be placed in an air-conditioned enclosure. The liquids and the elements can be kept in ideal conditions for, respectively, their analysis and their use.

Additionally, the invention further comprises an automatic analysis machine, in particular an automatic blood analysis machine containing a syringe block according to the invention.

Other characteristics and advantages of the invention will emerge from the following description, relating to non-limiting examples.

In the attached drawings:

FIG. 1 is a perspective view of a syringe block according to the invention;

FIG. 2 is a part of a collector for a syringe block according to the invention;

FIG. 1 represents a syringe block 1, provided to be integrated in an automatic blood analysis machine.

It comprises a set of six syringes 11-16 arranged in parallel, the casings of which are all formed in a single, more or less parallelepipedic casing piece 2. The casings are arranged vertically, such that a respective piston 21-26 (see FIG. 3) slides across their respective lower extremity, across a lower face of the casing 2.

Figure 3:
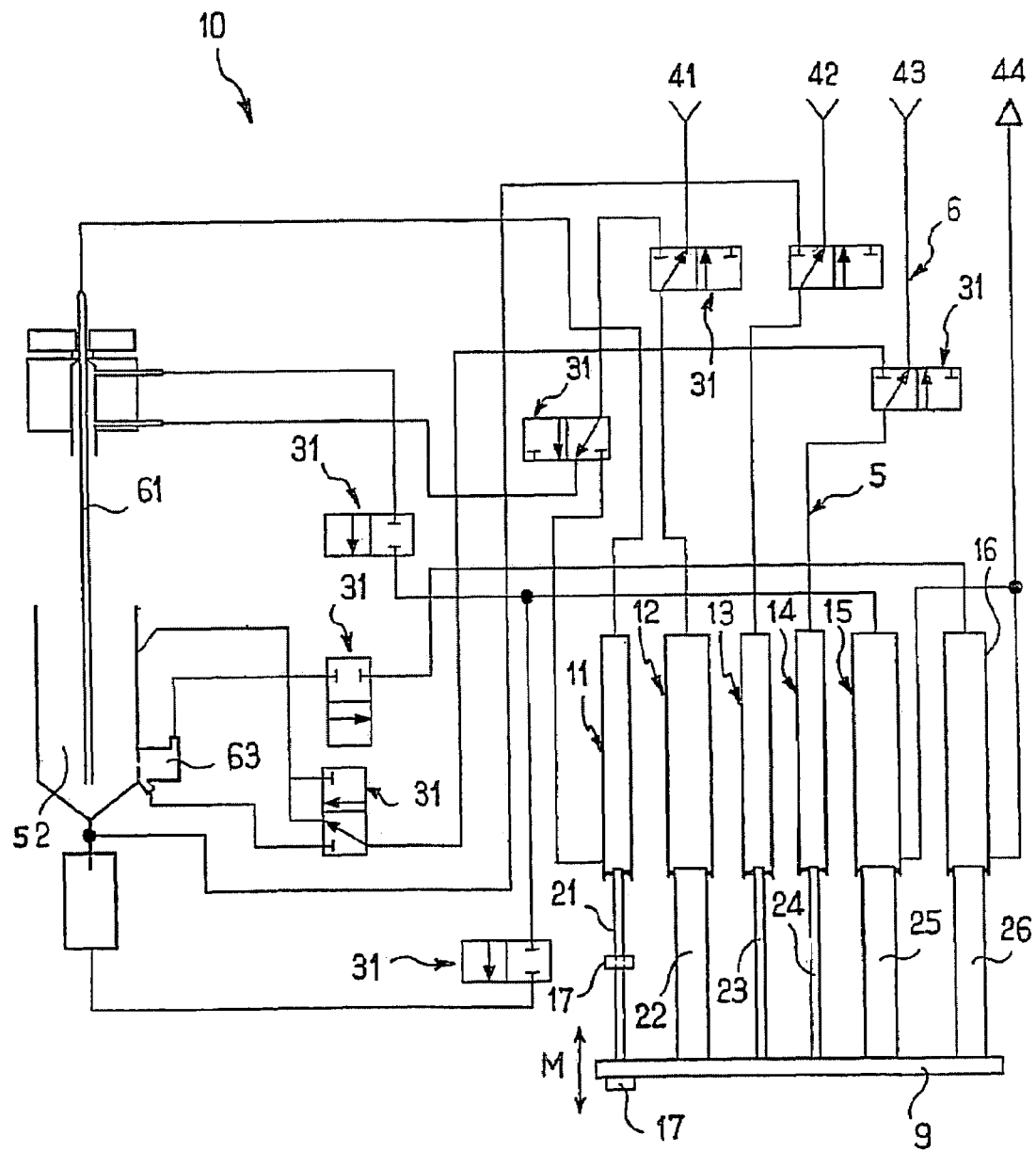
FIG. 3 is a block diagram of an automatic analysis machine according to the invention; and, FIG. 4 is a view of another embodiment of a syringe block.

In FIG. 1, the pistons are all rigidly fixed to a single clamp 9. The clamp is linked to a motor such that it can move all the pistons in a single movement M, here vertical translation, inside their respective casings. In FIG. 3, all the pistons are rigidly fixed to the clamp except for piston 21, which has two stops 17 for the clamp 9, one in each direction of translation according to movement M, thus defining dead travel for the piston 21 of the syringe 11.

The collector 3 has a base 4 more or less in the form of a parallelepiped. The casing piece is fixed by an upper surface against a lower face of the base 4. It comprises several electronic switch valves 31 fixed to the upper face of the said parallelepiped. The collector 3 also comprises, formed by moulding in the parallelepiped (see the piece in FIG. 2), a network 5,6 of ducts. This network comprises first, inside ducts 5, linking each syringe to at least one respective electronic switch valve. It also comprises second ducts 6, extending from the electronic switch valves towards, for example, containers for a sample to be analyzed (38), or towards containers for other liquids 41-43.

As illustrated in FIG. 2, the network is realized by moulding in the piece 8 forming part of the base 4. Another part, not shown, complementing the piece 8, completes the form of the ducts.

On its upper face, the collector 3 also serves as a support for the elements of the automatic analysis machine, in particular an optical bench 51, a dilution and counting vessel 52, an optical and resistivity measurement vessel 53, and an electronic card 54, used for analysis.

FIG. 3 will now be described in more detail, representing schematically the operation of an automatic analysis machine 10. The syringes 11-16 include a syringe 11 assigned to the taking of an untreated blood sample, that is to say as presented initially to the automated machine, using a needle 61, and to the cleaning of the needle.

The syringes also include a syringe 12 for the handling of a diluting product 41, a syringe 13 for the handling of a lytic product 42, a syringe 14 for the handling of a cleaning product 43, and two syringes 15,16, coupled so as to form an air pump, specially assigned to the removal of waste 44, during or at the end of the analysis.

The untreated sample is introduced into the automated machine using the needle 61, then placed by this needle into a tank 52, serving in particular to dilute it. The syringes 15, 16 forming the air pump, can in particular be used to take a sample from a receptacle 63, communicating direct with the tank 52, with a view to a counting. This sampling is carried out by creating a depression inside the receptacle 63 using the air pump.

Instead of a depression, the air pump can also be used to create an excessive pressure, for example to ensure the homogenization of a mixture.

The different positions of the electronic switch valves allow the user to carry out a task with one of the syringes while the others have a neutralized function, although the respective pistons of these other syringes are led to carry out a single movement M with the said one syringe.

Figure 4:
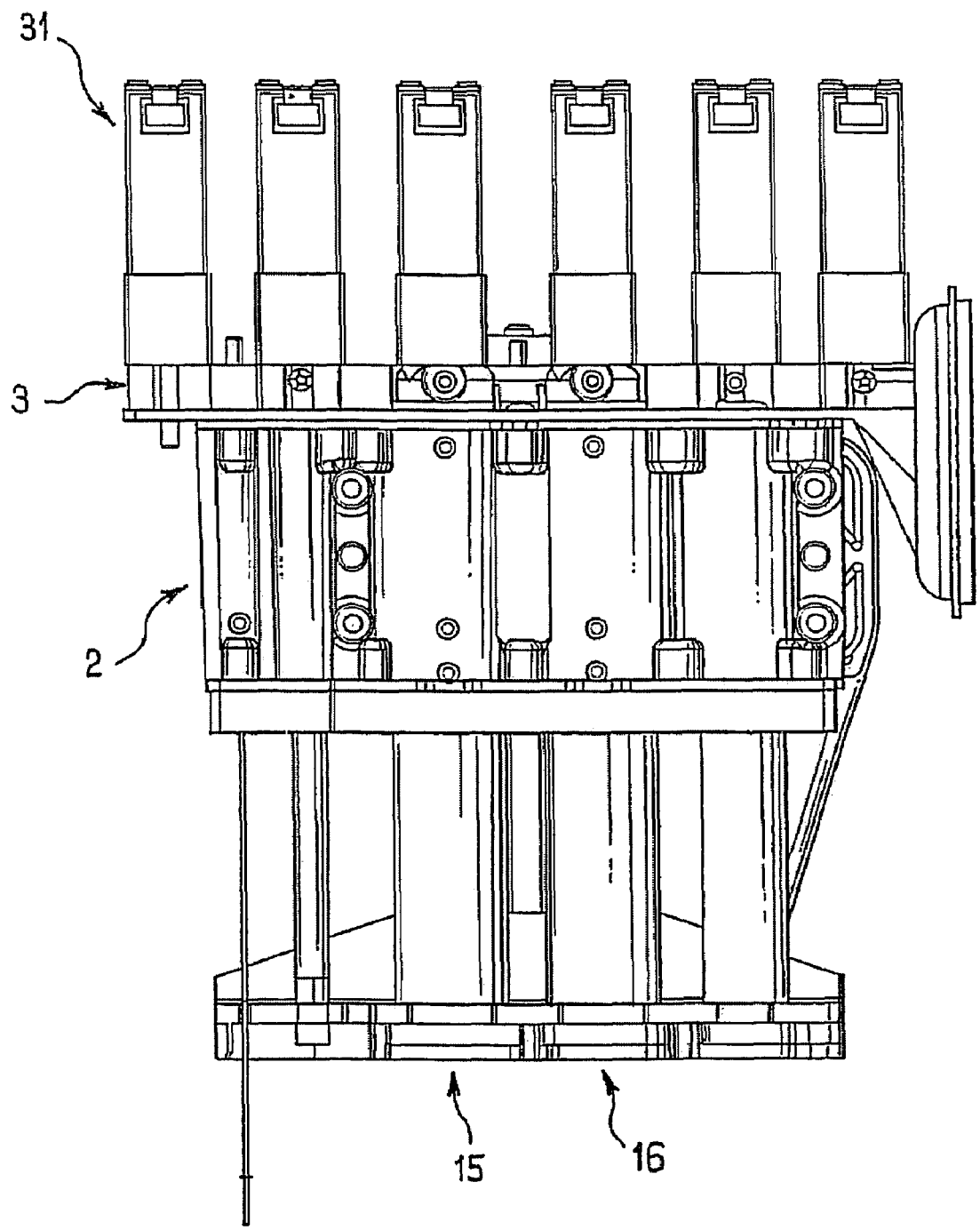

The syringe block of the FIG. 4 is a lighter embodiment than the syringe block in FIG. 1. It comprises a collector 3, supporting six electronic switch valves 31 and five syringes 2, of which two syringes 15,16 form an air pump.

The invention is of course not limited to the examples which have just been described and numerous adjustments can be made to these examples without going beyond the scope of the invention.

In particular, the different parts and elements of the invention can differ in number and form from what has been described, as long as this does not affect their operation.

The first and/or second ducts can be reduced to simple holes, of sufficient thickness to cross a part of the collector linking, for example, an electronic switch valve and an associated syringe.

The first and/or second ducts can be realized by any other means other than machining or moulding. Instead of forming only a single layer of ducts between two complementary pieces, they can also form several layers of ducts placed one on top of another and separated two-by-two by an adapted piece, in which one of the two thus-separated layers can be realized.

The invention claimed is:

1. A syringe block (10), adapted to be used in an automatic liquid-sample analysis machine (1), said block comprising a collector (3) and plural syringes (11-16) among which:
   a first one of said plural syringes takes an untreated blood sample,
   a second one of said plural syringes handles a diluting product (41),
   a third one of said plural syringes handles a lytic product (42),
   a fourth one of said plural syringes handles a cleaning product (43), and
   at least a fifth one of said plural syringes forms an air pump,
   each syringe of said plural syringes comprising a casing and a piston (21-26) between which is defined an internal volume,
   said collector comprising electronic switch valves (31), first ducts (5) linking the electronic switch valves directly to the respective internal volumes and second ducts (6) extending from the electronic switch valves in the direction of respective containers for liquids (41-44),
   wherein the pistons of all the plural syringes are rigidly linked to each other such that they simultaneously carry out a single movement (M) inside their respective casings, different positions of the electronic switch valves enabling a task to be carried out with one of said plural syringes, while others of said plural syringes have a neutralized function, although respective pistons of said others of said plural syringes carry out the single movement with said one of said plural syringes, the casings of all of the plural syringes being mounted directly on the collector (3).

2. The syringe block according to claim 1, wherein the air pump comprises at least two syringes (15,16).

3. The syringe block according to claim 1, wherein the collector comprises one or more pieces (8) in which the first and/or second ducts are realized.

4. The syringe block according to claim 1, wherein the air pump is used to create a depression for the taking of a sample.

5. The syringe block according to claim 1, wherein the air pump is used for the removal of waste (44)

6. The syringe block according to claim 1, wherein said syringe block comprises at least one dilution chamber, which may be fixed on the collector and/or linked directly to a respective electronic switch valve by a duct among the second ducts.

7. The syringe block according to claim 1, wherein said syringe block comprises at least a measurement chamber, which may be fixed on the collector and/or linked direct to a respective electronic switch valve by a duct among the second ducts.

8. A syringe block according to claim 1, wherein the syringe block comprises at least an incubation chamber, which may be fixed on the collector and/or linked directly to a respective electronic switch valve by a duct among the second ducts.

9. The syringe block according to claim 1, wherein the syringe block comprises at least a hydraulic circulation vessel, which may be fixed on the collector and/or linked directly to a respective electronic switch valve by a duct among the second ducts.

10. The syringe block according to claim 1, wherein the syringe block comprises at least an optical bench (51), which may be fixed on the collector and/or linked directly to a respective electronic switch valve by a duct among the second ducts.

11. The syringe block according to claim 1, wherein the syringe block comprises at least a card (54) carrying electronic circuits, said electronic circuits being used in the analysis when said block is used in an automatic analysis machine.

12. The syringe block according to claim 1, wherein said syringe block further comprises an air-conditioned enclosure.

13. An automatic analysis machine (10), comprising the syringe block (1) according to claim 1.

14. A syringe block (10), adapted to be used in a automatic liquid-sample analysis machine (1), said block comprising:
   plural syringes (11-16), each of said plural syringes comprising a casing and a piston (21-26) between which defines an internal volume; and
   a collector (3), said collector comprising electronic switch valves (31), first ducts (5) linking the electronic switch valves directly to respective internal volumes and second ducts (6) extending from the electronic switch valves in a direction of respective containers for liquids (41-44),
   said block further comprising an air pump;
   wherein at least one of the plural syringes forms the air pump and the pistons of all the plural syringes are rigidly linked to each other such that they simultaneously carry out a single movement (M) inside their respective casings,
   the collector (3) having a base (4), the casings of all the syringes being formed in a single casing element (2) mounted directly by an upper surface of the casing element against a lower face of the base (4), the electronic switch valves (31) being fixed to an upper face of the base (4).

15. The syringe block according to claim 14, wherein the collector (3) further comprises a network (5,6) of molded inside ducts, formed in the base.

16. The syringe block according to claim 15, wherein the inside ducts are the first ducts.

17. A syringe block, adapted to be used in an automatic liquid-sample analysis machine, said block comprising:
   plural syringes, each of said syringes comprising a casing and a piston between which is defined an internal volume;
   a collector, said collector comprising electronic switch valves, first ducts linking the electronic switch valves directly to a corresponding internal volume and second ducts extending from the electronic switch valves in a direction of respective containers for liquids handled by said syringes,
   an air pump, at least one of the plural syringes comprising the air pump, pistons of all the plural syringes are rigidly linked to each other and are configured to simultaneously carry out a single movement in a common direction inside respective casings.

18. The syringe block according to claim 17, wherein the air pump comprises two syringes having a common inlet and separate outlets.

* * * * *